US012714831B2

(12) United States Patent
Wilke et al.

(10) Patent No.: US 12,714,831 B2
(45) Date of Patent: Aug. 25, 2026

(54) TWO-PART WOUND DRESSING

(71) Applicant: Mayo Foundation for Medical Education and Research, Rochester, MN (US)

(72) Inventors: Julia Wilke, Ponte Vedra Beach, FL (US); Benjamin Wilke, Ponte Vedra Beach, FL (US); Mathew Thomas, Ponte Vedra Beach, FL (US); Jim Jeter, Jacksonville, FL (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 86 days.

(21) Appl. No.: 18/680,583

(22) Filed: May 31, 2024

(65) Prior Publication Data

US 2025/0367409 A1 Dec. 4, 2025

(51) Int. Cl.

| | |
|---|---|
| ***A61F 13/00*** | (2024.01) |
| ***A61F 13/02*** | (2006.01) |
| ***A61F 13/0203*** | (2024.01) |
| ***A61L 15/26*** | (2006.01) |
| ***A61L 15/60*** | (2006.01) |
| ***A61M 1/04*** | (2006.01) |
| ***A61M 25/02*** | (2006.01) |

(52) U.S. Cl.

CPC ......... *A61M 25/02* (2013.01); *A61F 13/0213* (2013.01); *A61F 13/0263* (2013.01); *A61L 15/26* (2013.01); *A61L 15/60* (2013.01); *A61M 1/04* (2013.01); *A61F 2013/00412* (2013.01); *A61F 2013/00553* (2013.01); *A61F 2013/00604* (2013.01); *A61F 2013/0074* (2013.01); *A61M 2025/0273* (2013.01)

(58) Field of Classification Search

None

See application file for complete search history.

(56) References Cited

U.S. PATENT DOCUMENTS

| | | | | |
|---|---|---|---|---|
| 4,909,244 A * | 3/1990 | Quarfoot | A61F 13/023 | 428/319.3 |
| 4,917,112 A * | 4/1990 | Kalt | A61F 13/023 | D24/189 |
| 5,000,741 A * | 3/1991 | Kalt | A61M 16/047 | 128/207.29 |
| 5,308,339 A * | 5/1994 | Kalt | F16L 3/08 | 128/DIG. 26 |
| 6,255,552 B1 | 7/2001 | Cummings et al. | | |
| 8,710,289 B2 * | 4/2014 | Russell | A61F 13/0213 | 602/41 |
| 2009/0216168 A1 | 8/2009 | Eckstein | | |

(Continued)

FOREIGN PATENT DOCUMENTS

| | | |
|---|---|---|
| CN | 203873967 U | 10/2014 |
| CN | 204428271 U | 7/2015 |

*Primary Examiner* — Kim M Lewis

(74) *Attorney, Agent, or Firm* — SALIWANCHIK, LLOYD & EISENSCHENK

(57) ABSTRACT

A sterile two-part wound dressing for surgical drainage tube and chest thoracostomy tubes that is designed to create a seal around the chest tube during tube removal decreasing the risk of air leak and post-pull iatrogenic pneumothorax, to absorb exudate from the wound, and to provide a water-resistant covering to limit contamination of the wound during healing.

19 Claims, 11 Drawing Sheets

(56) References Cited

U.S. PATENT DOCUMENTS

| | | | | |
|---|---|---|---|---|
| 2011/0295173 | A1* | 12/2011 | Wright | A61F 13/023<br>602/54 |
| 2018/0021177 | A1 | 1/2018 | Bedford et al. | |
| 2020/0246192 | A1* | 8/2020 | Hoggarth | A61F 13/0246 |
| 2022/0184294 | A1* | 6/2022 | Locke | A61M 1/915 |

* cited by examiner

TWO-PART WOUND DRESSING

BACKGROUND OF THE INVENTION

Chest drainage tubes are frequently placed to drain fluid and air from the intrapleural space and allow expansion of the lungs. During tube removal there is a risk that air may re-enter the cavity through the tube entry site at the skin when the tube is withdrawn. When this occurs, the lung may partially or completely collapse, a phenomenon known as a "post-pull pneumothorax". Development of a collapsed lung following chest drainage tube removal is reported to occur in up to 30% of patients; 20% of whom will require placement of a new chest tube. This has been reported as the most significant complication following chest tube removal and is associated with increased patient morbidity, hospital length of stay, and increased risk for hospital readmission.

Despite the known high rate of post-pull pneumothorax, there have been no significant improvements in dressing design to reduce the risk of air exchange between the external environment and lung cavity during tube removal. The problem is largely due to the current method for bandaging the chest tube entry site. While several dressing iterations have been recommended in the literature, there is no universally accepted dressing or method for removing chest tubes. The most common dressing, which has been in use for almost 100 years, is a bandage created at the bedside using petroleum gauze covered by 4×4" gauze and tape. The integrity of these simple bandages is variable, dependent on the creator, and often not sufficiently airtight. Therefore, there is a need for a standardized dressing with superior sealing and absorption qualities, and improved bandage design to reduce the risk of complications, to increase patient safety, and improve the quality of care.

BRIEF SUMMARY OF THE INVENTION

The subject invention pertains to a two-part wound dressing for use with a surgical drainage tube. The two-part wound dressing comprises a top dressing layer and a bottom dressing layer, where the two-part wound dressing includes a top dressing layer comprising (a) a removable first top dressing release liner, (b) a top dressing cover, (c) a top dressing closed cell foam, and (d) a second top dressing release liner; and a bottom dressing layer comprising (c) a bottom closed cell dressing foam, (f) a first bottom dressing hydrogel (g) a bottom dressing closure carrier, (h) a second bottom dressing hydrogel, and (i) a bottom dressing release liner.

In some aspects, the subject invention discloses a sterile two-part wound dressing where the bottom dressing layer includes a highly absorbent material adapted for absorbing exudate that passes through the bottom dressing layer, and the top dressing layer and the bottom dressing layer include an airtight and waterproof sealing material adapted to conform around a surgical tube or chest thoracostomy tube and create an air-tight seal when the surgical tube or chest thoracostomy tube is removed.

In embodiments, each element of the bottom dressing layer, including a bottom dressing closed cell foam, a first bottom dressing hydrogel, a bottom dressing closure carrier, a second bottom dressing hydrogel, preferably has an approximately round or oval shape and comprises a slit, where in a length of each slit is from about 50% to 80% of the diameter of the respective layer and a width from about 0.01 mm to about 2 mm, and the length of the slit preferably has constant length through the different elements of the bottom dressing layer.

In other aspects, the subject invention discloses a method for using a sterile surgical tube dressing, comprising applying the two-part wound dressing to a surgical tube wound, where the two-part wound dressing includes a top dressing layer, a bottom dressing layer, and a removable combined liner between the top dressing layer and the bottom dressing layer, where the two-part wound dressing includes a top dressing closed cell foam and a bottom dressing closed cell foam, where the top dressing closed cell foam and a bottom dressing closed cell foam are independently wrapped around a surgical tube to form an air-tight seal during surgical tube removal, and where the bottom dressing layer comprises a first and a second bottom dressing hydrogel, comprising a highly absorbent material for absorbing exudate from the wound.

In embodiments, the bottom dressing release liner is removed and the dressing is wrapped around the surgical tube through the slits present in each element of the bottom dressing, including the bottom dressing closed cell foam, the first bottom dressing hydrogel, the bottom dressing closure carrier, the second bottom dressing hydrogel.

In preferred embodiments, the surgical tube is a chest thoracostomy tube.

In preferred embodiments, the top dressing layer is replaceable.

In some embodiments, the bottom dressing layer is pulled under tension when applied to the wound to approximate the skin edges of the wound and seal the wound to promote wound healing.

In some embodiments, the top dressing closed cell foam and the bottom dressing closed cell foam are adapted to provide an air-tight seal over the wound that inhibits air exchange after chest thoracostomy tube removal.

In preferred embodiments, the top dressing closed cell foam, the bottom dressing closed cell foam and the first and second bottom dressing hydrogel form an airtight and watertight seal around the surgical tube. The first and second bottom dressing hydrogel improve the seal by absorbing exudate and swelling with the fluids from the exudate.

In more preferred embodiments, the airtight seal around the chest thoracostomy tube significantly reduces the risk for post-pull iatrogenic pneumothorax.

DETAILED DISCLOSURE OF THE INVENTION

Selected Definitions

Figure 1A:
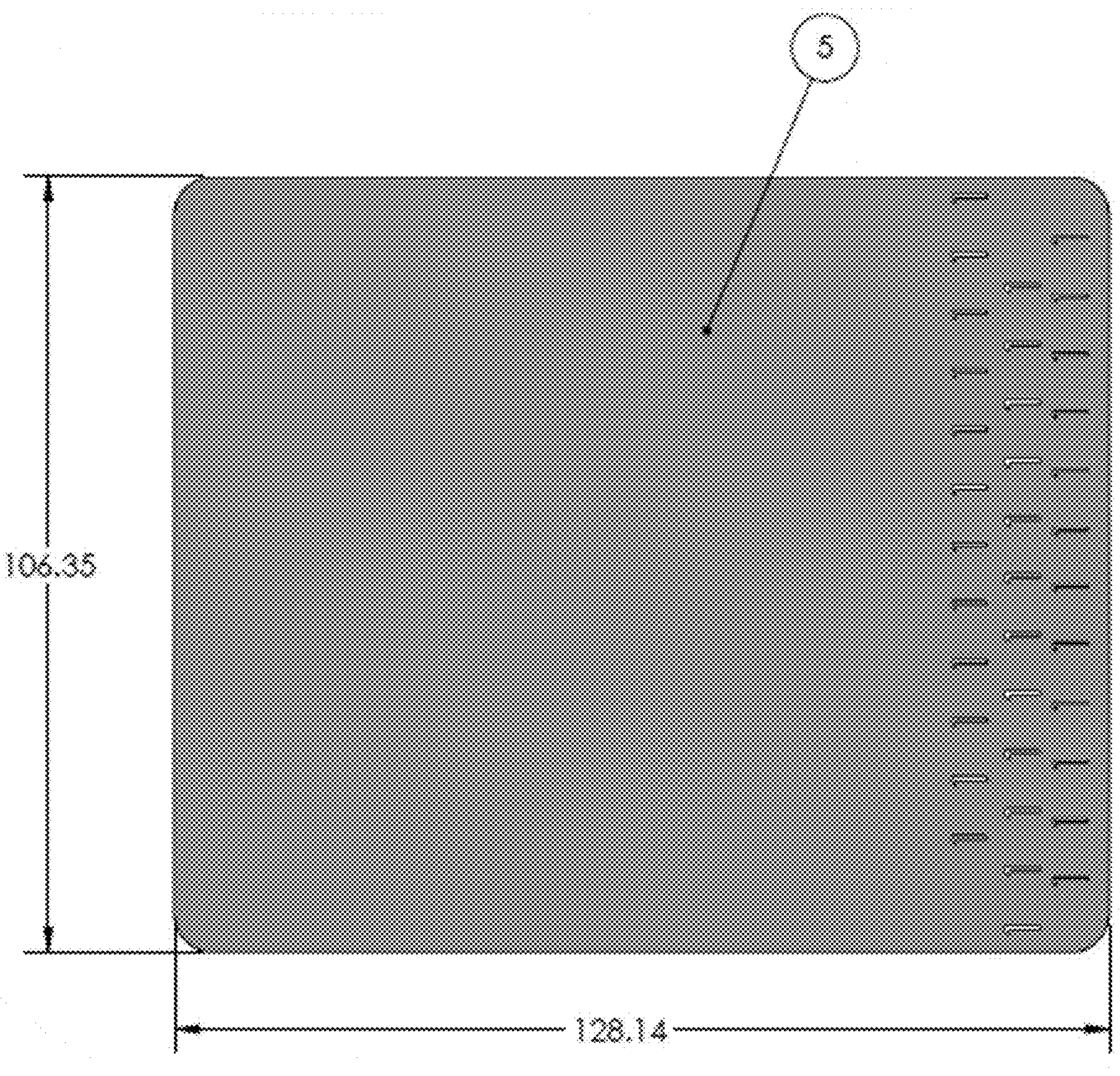
FIGS. 1A-1J are schematic illustrations of the components of the two-part wound dressing.
Figure 1B:
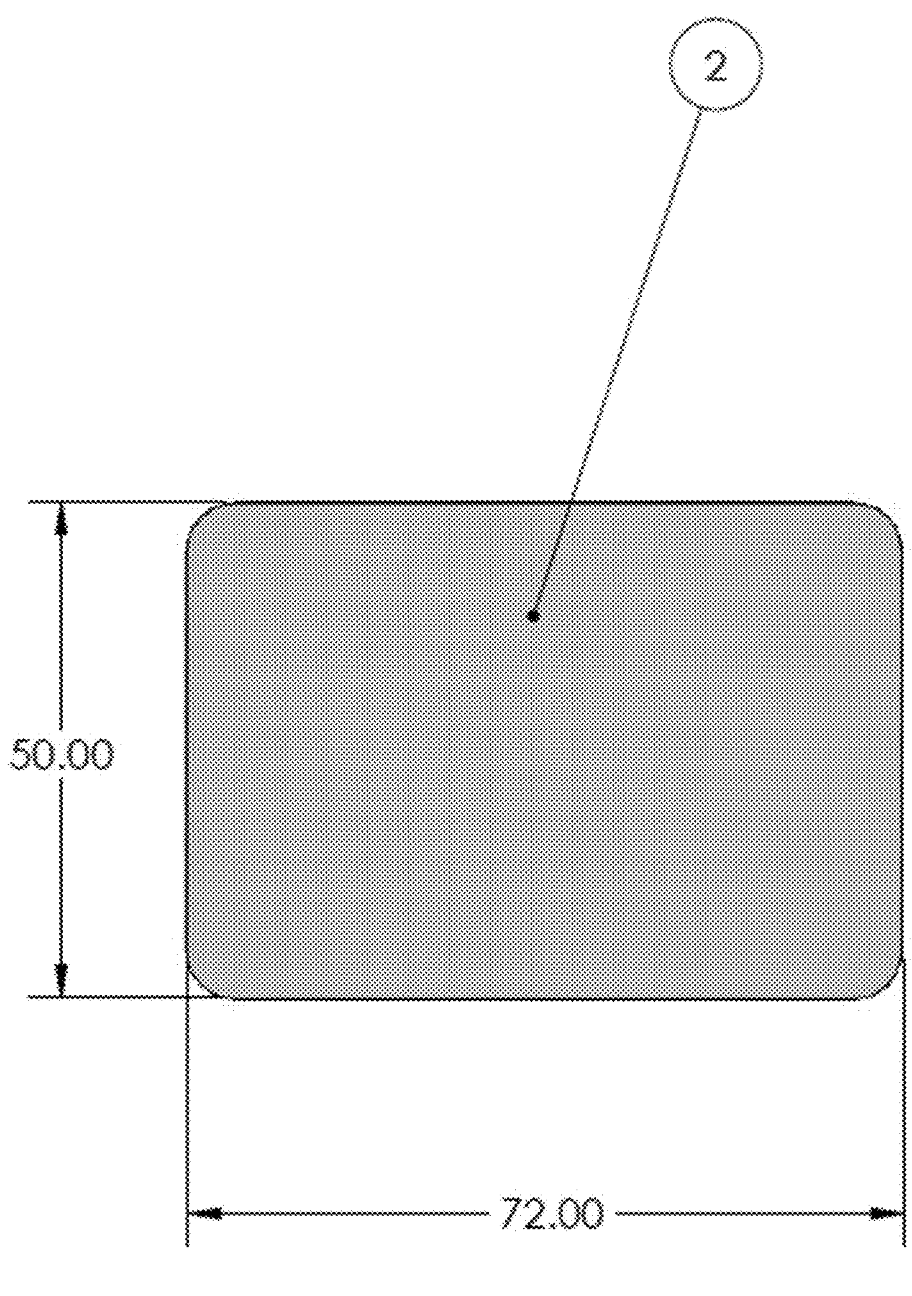
Figure 1C:
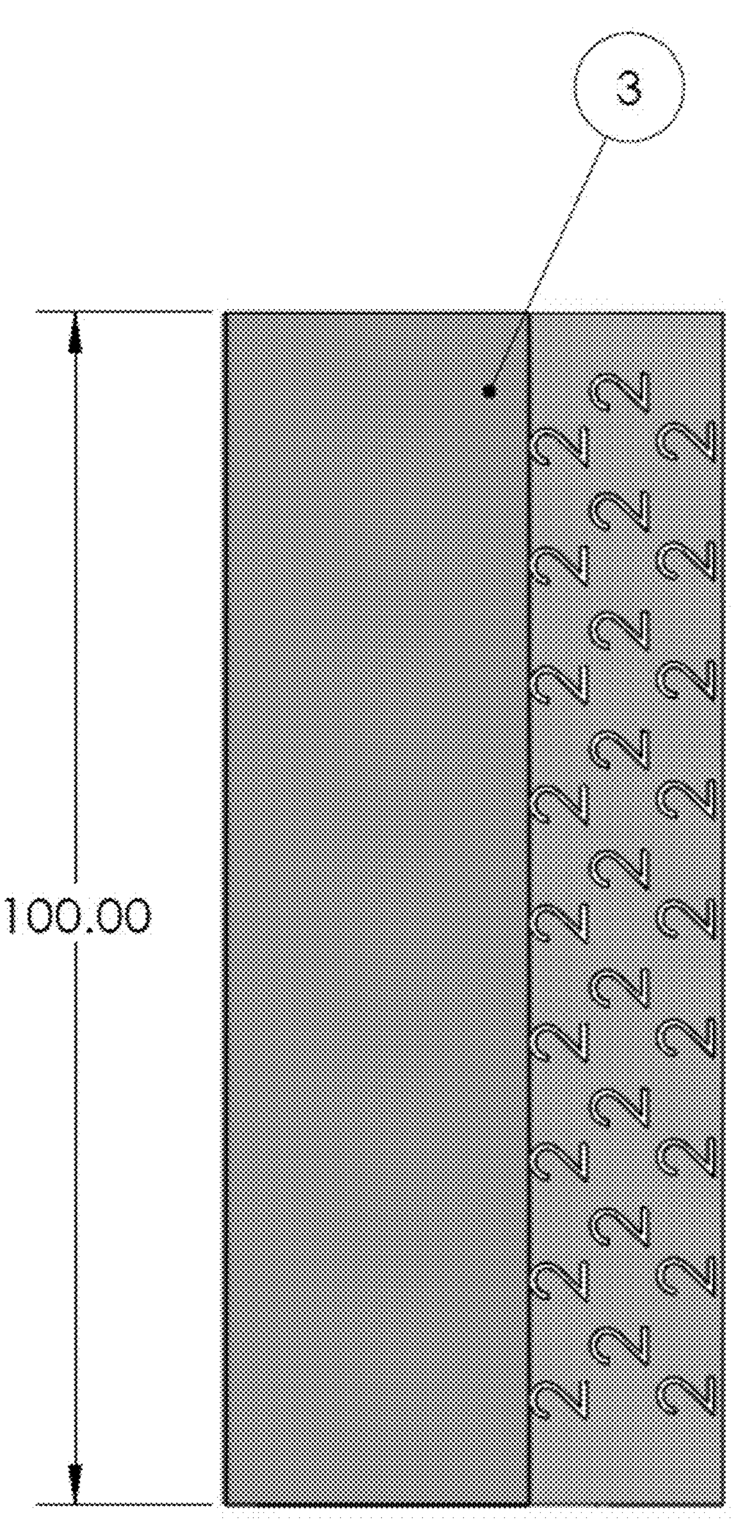
Figure 1D:
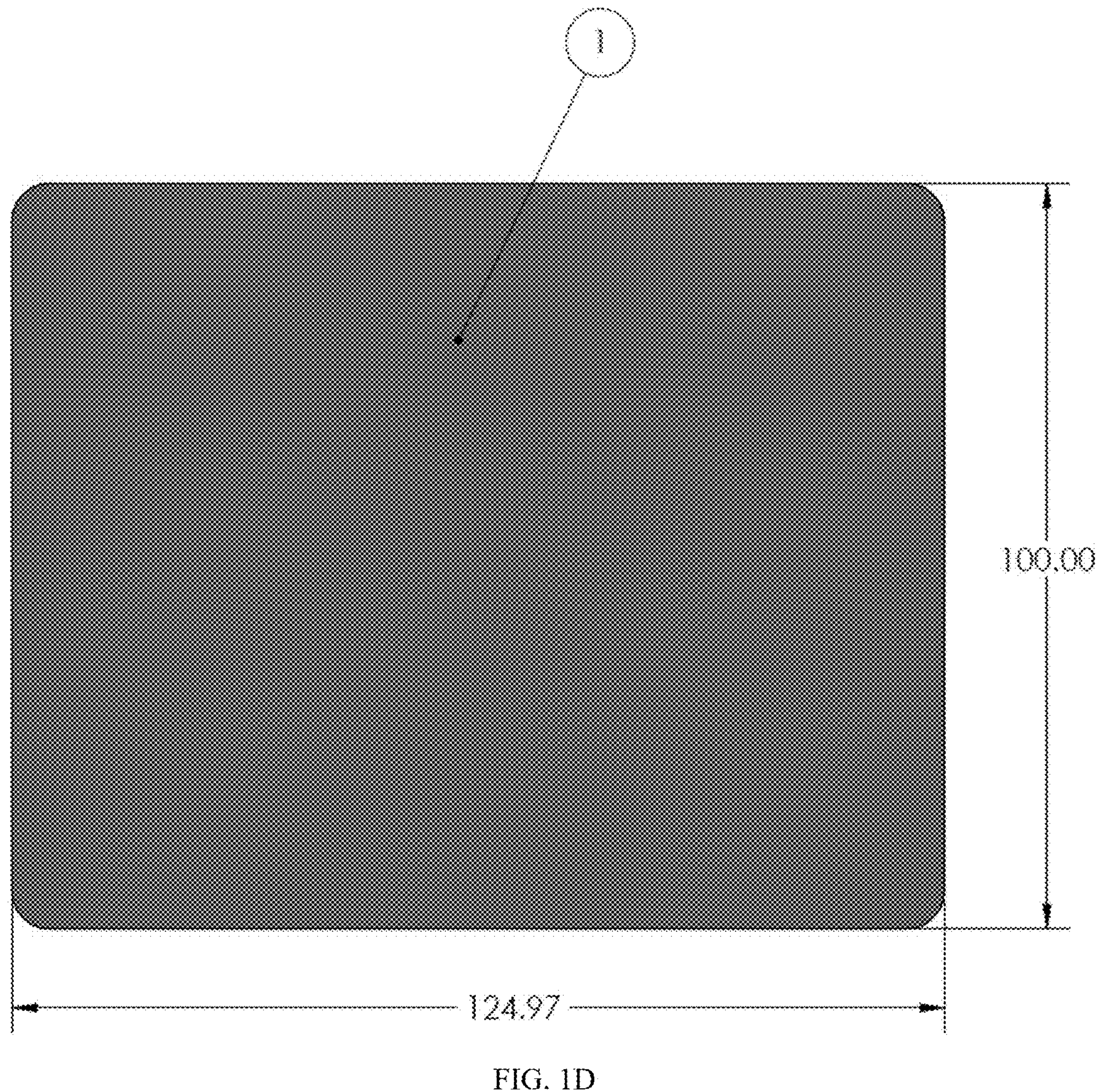
Figure 1E:
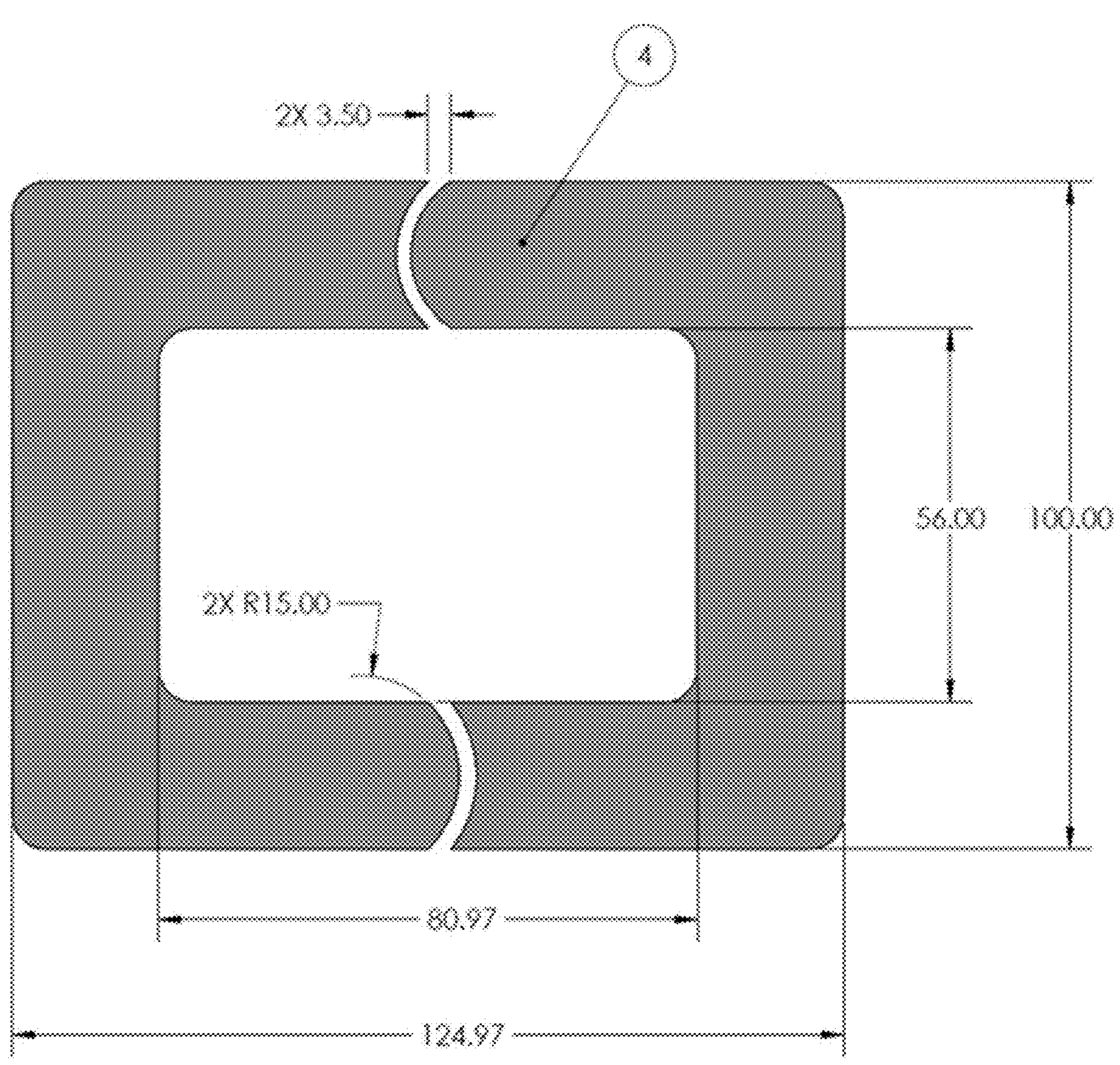
Figure 1F:
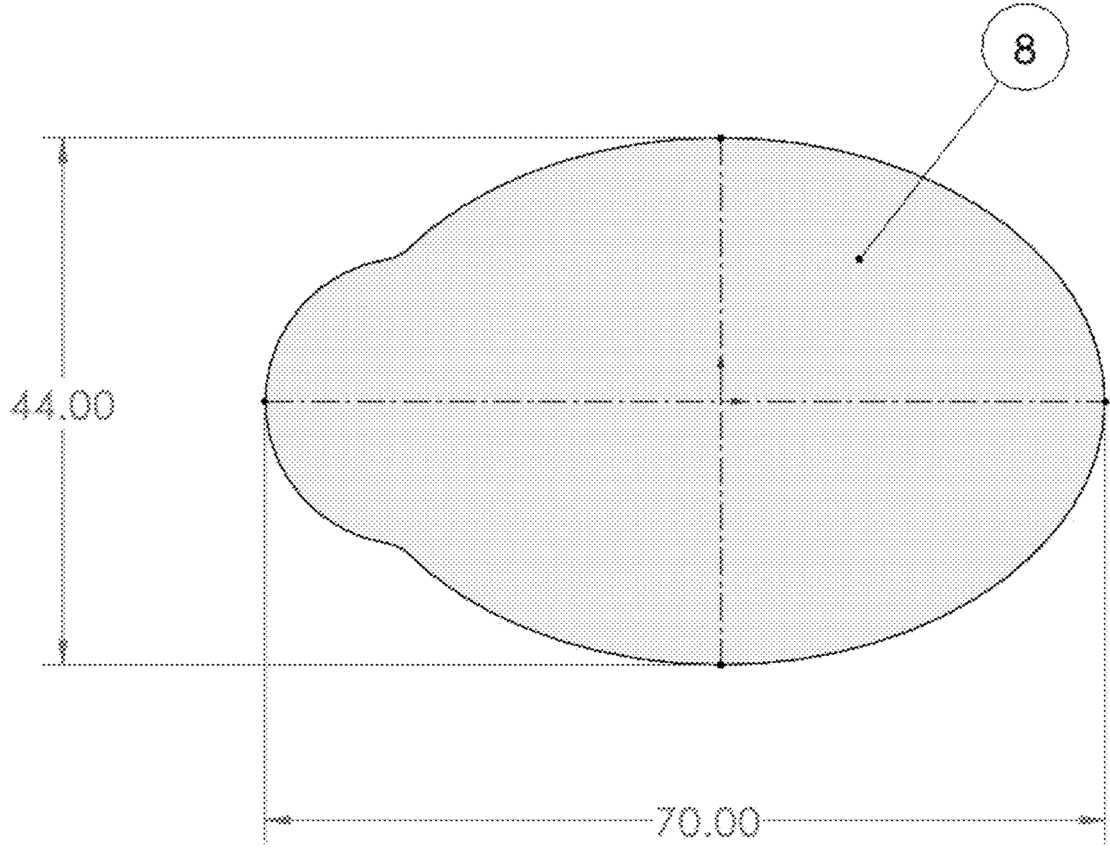
Figure 1G:
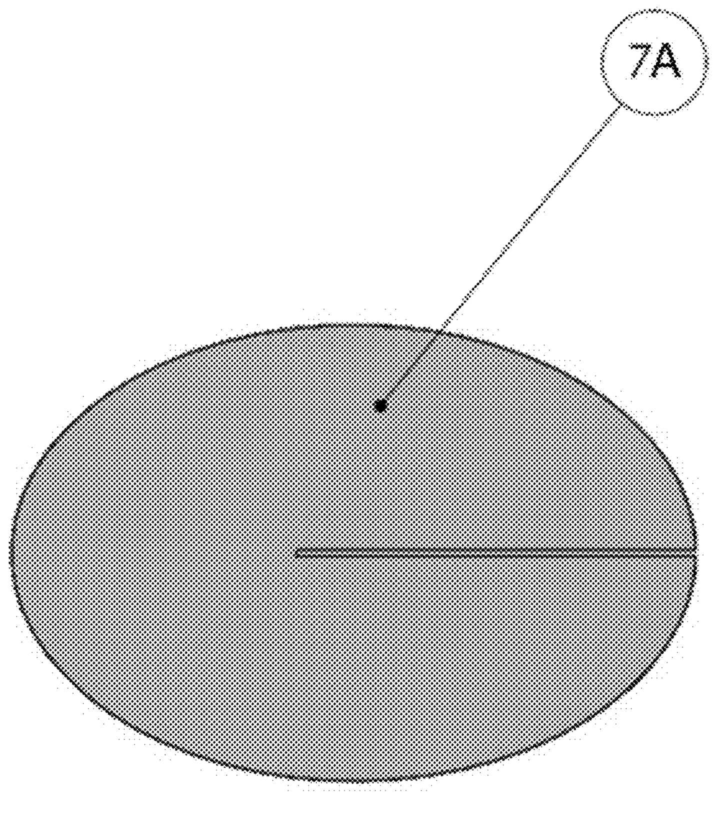
Figure 1H:
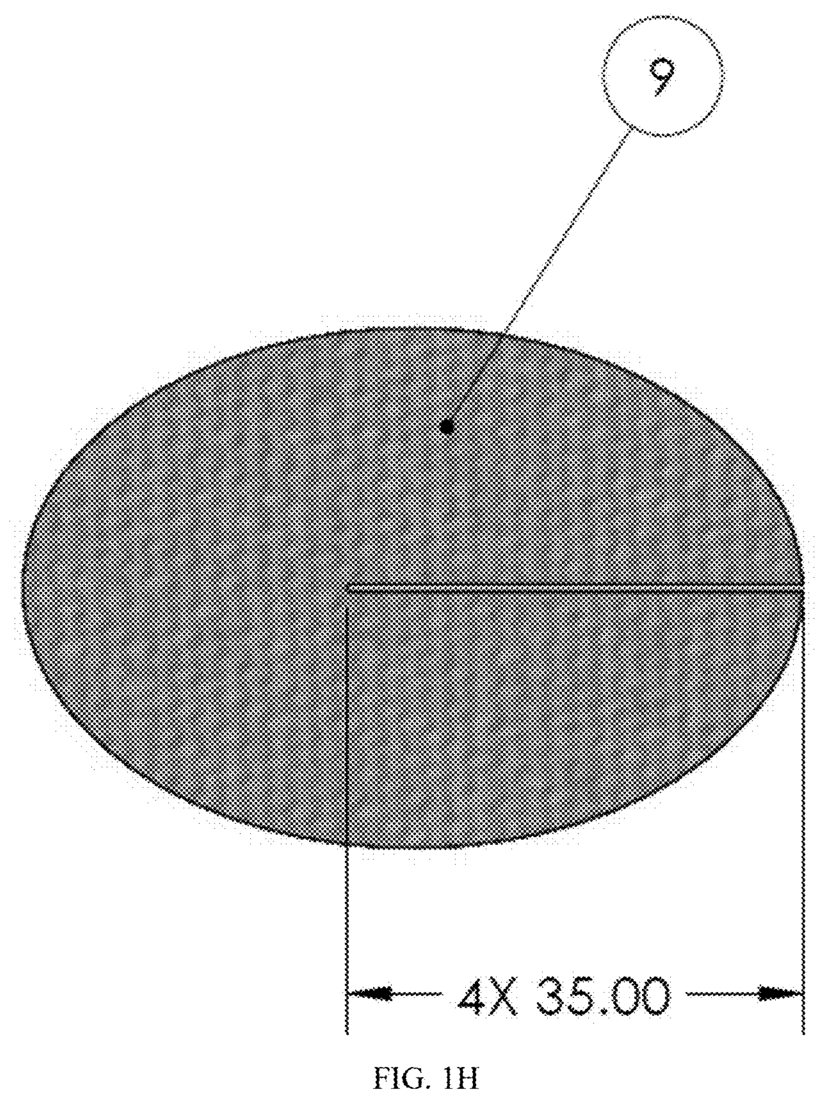
Figure 1I:
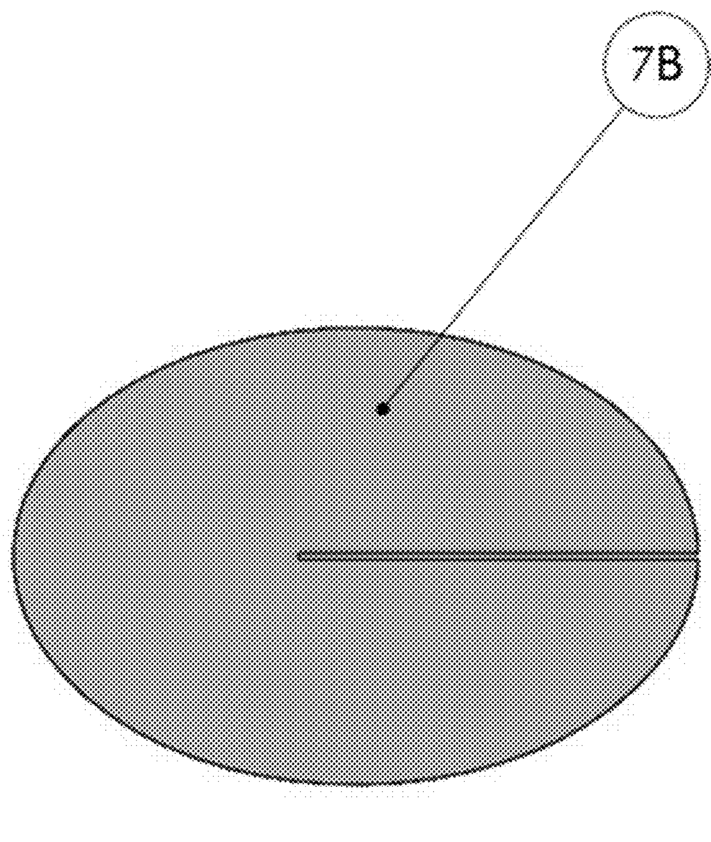
Figure 1J:
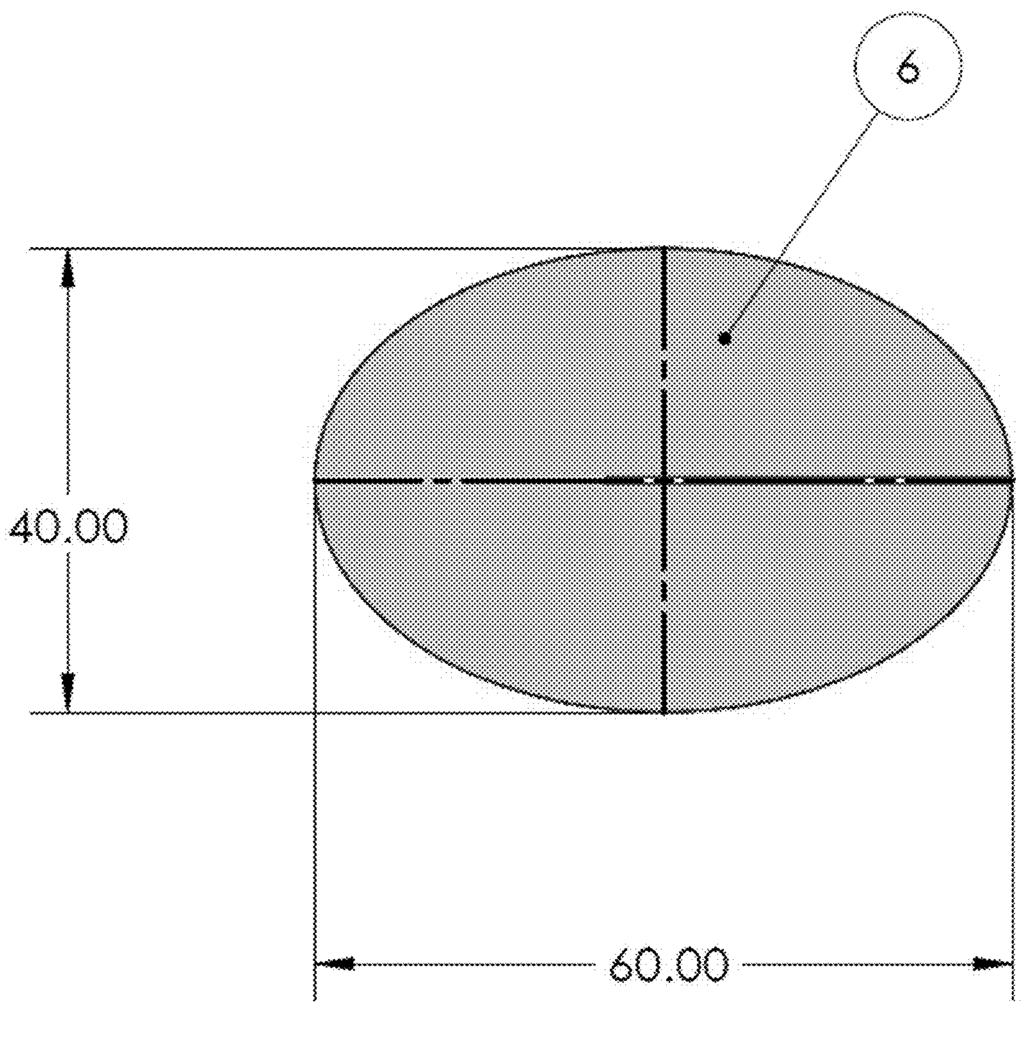
Figure 2:
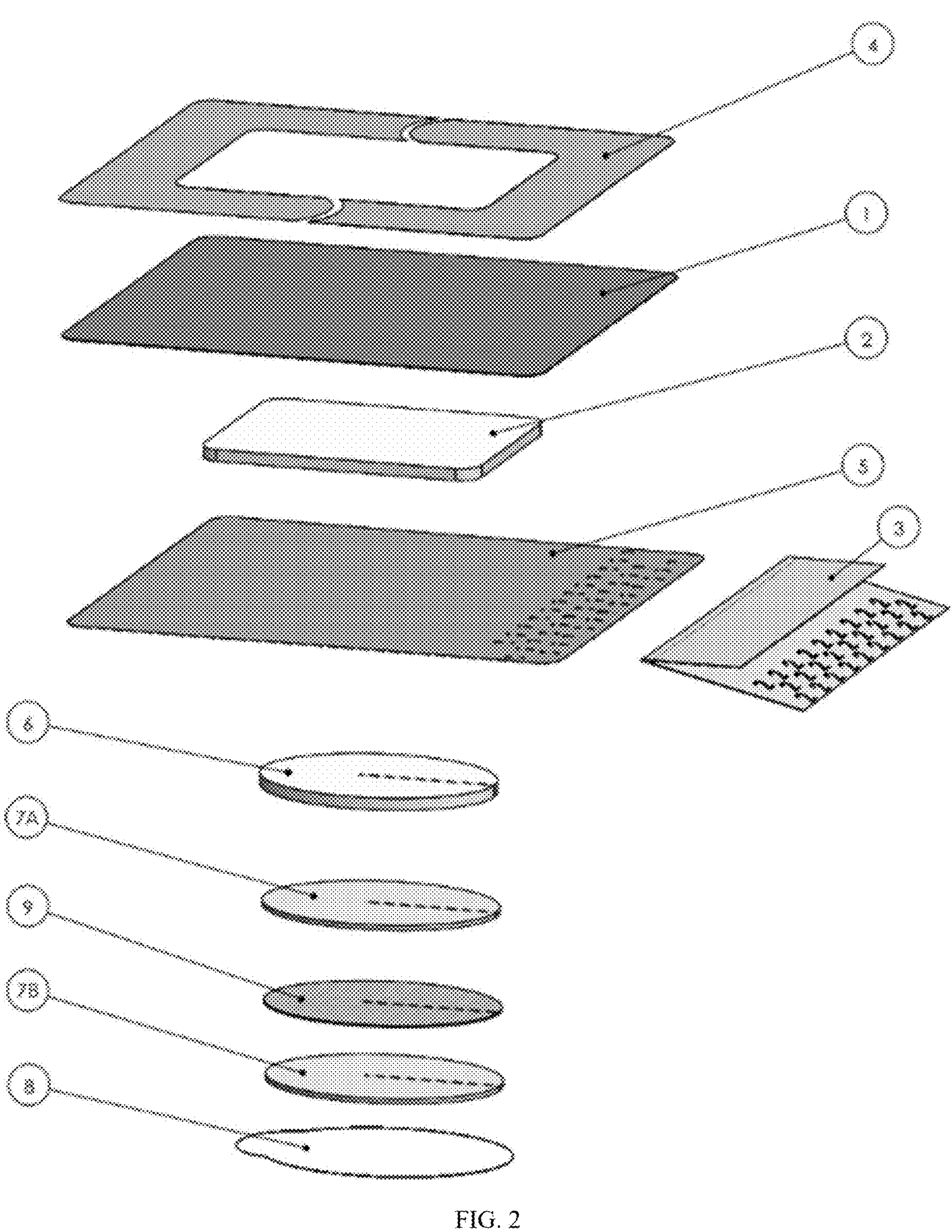
FIG. 2 is a schematic illustration of an exploded cross section of the two-part wound dressing.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising". The transitional terms/phrases (and any grammatical variations thereof) "comprising", "comprises", "comprise", "consisting essentially of", "consists essentially of", "consisting" and "consists" can be used interchangeably.

The term "about" means within an acceptable error range for the particular value as determined by one of ordinary skill in the art, which depends in part on how the value is measured, i.e., the limitations of the measurement system. In the context of compositions containing amounts of ingredients where the term "about" is used, these compositions contain the stated amount of the ingredient with a variation (error range) of 0-10% around the value (X±10%). In other contexts, the term "about" is providing a variation (error range) of 0-10% around a given value (X±10%). As is apparent, this variation represents a range that is up to 10% above or below a given value, for example, X±1%, X±2%, X±3%, X±4%, X±5%, X±6%, X±7%, X±8%, X±9%, or X±10%.

Other features and advantages of the invention will be apparent from the following description of the preferred embodiments thereof, and from the claims.

All references cited herein are hereby incorporated by reference in their entirety.

Product Description

The present invention relates to a novel wound dressing for use with a surgical tube, and especially with a surgical drainage or chest thoracotomy tube. The dressing is a sterile two-part dressing. The wound dressing comprises two parts: a bottom layer comprising a highly absorbent closed cell foam pad and hydrogel to facilitate a reliable seal over a wound or skin incision, inhibiting air or fluid exchange after tube removal. The hydrogel portion (Polymer Science product P-DERM® PS-1446) contains two 0.75 mm thick hydrogel sheets, with a carrier liner sandwiched between for tensile support (Vilmed M1670). The hydrogel functions as an adhesive to adhere the lower layer to the skin. The hydrogel will swell when exposed to bodily fluids, forming an air and watertight seal over the incision.

On top of the hydrogel layers is a closed cell foam (in an embodiment, Freudenberg 3 mm foam). The hydrogel acts as an adhesive to hold the foam in place. The foam is a material that limits air flow (closed cell design), while contouring to multiple tube sizes.

The top dressing comprises an absorbent closed cell foam pad (in an embodiment, Freudenberg 3 mm foam) and polyurethane film with high tack acrylate adhesive (in an embodiment, Product 3M 9833). Together the bottom and top closed cell foam layers form a circumferential airtight seal around the tube during removal; in the case of removal of a thoracostomy tube, decreasing the risk for an iatrogenic pneumothorax. The acrylic adhesive adheres the top layer foam to the polyurethane covering and secures the polyurethane dressing to the skin, which contributes to the water-resistant properties of the dressing. A stiffener is present on the polyurethane to maintain the shape of the dressing during application, inhibiting wrinkles that may allow airflow into the dressing. The stiffener is cut out from the carrier paper associated with the polyurethane, during manufacturing. Finally, a release liner (for example, Fox River Product 315) is used to cover and protect all adhesive surfaces.

Referring to the figures for reference, the sterile wound dressing of the subject invention comprises two parts, a top dressing layer and a bottom dressing layer. The top dressing layer comprises a first top dressing release liner 4; a top dressing cover 1, a top dressing closed cell foam 2; and a second top dressing release liner 3. The second top dressing release liner 3 protects the adhesive of the top dressing from sticking to the chest tube during tube removal. Once the tube is pulled, the second top dressing release liner 3 is removed and the dressing is fully applied. The bottom dressing layer comprises a bottom dressing closed cell foam 6, a first bottom dressing hydrogel 7A; a bottom dressing closure carrier 9; a second bottom dressing hydrogel 7B; and a bottom dressing release liner 8. The dressing further comprises a combined liner 5 between the top dressing layer and the bottom dressing layer, where the combined liner 5 is removed prior to placing the top dressing over the bottom dressing.

Each element of the bottom dressing layer, including the bottom dressing closed cell foam 6, the first bottom dressing hydrogel 7A, the bottom dressing closure carrier 9, the second bottom dressing hydrogel 7B, and the bottom dressing release liner 8, preferably has an approximately round or oval shape and each, except the bottom dressing release liner 8, comprises a slit, where in a length of each slit is from about 50% to 80% of the diameter of the respective layer and a width from about 0.01 mm to about 2 mm, and further the length of the slit preferably has consistent length through the different elements of the bottom dressing layer.

The top dressing release liner 4 is a stiffener that comprises a removable carrier paper, contacting and overlapping with a border section of the top dressing cover 1 during application of the two-part wound dressing. The top dressing release liner 4 is removed after application of the two-part dressing.

The top dressing cover 1 comprises a water-resistant cover that includes an adhesive portion on the underside. The top dressing cover 1 is the outermost portion of the two part dressing and is disposed over the top dressing closed cell foam 2.

The top dressing closed cell foam 2 comprises a closed cell foam, where the closed cell foam includes an airtight and absorbent sealing material. The top dressing closed cell foam 2 is disposed around a surgical tube, for example, a drainage or the thoracostomy tube. The top dressing closed cell foam 2 is disposed at the interface between the top dressing cover 1 and the first bottom dressing closed cell foam 6.

The top dressing closed cell foam 2 and the bottom dressing closed cell foam 6 form an airtight seal during tube removal. The second top dressing release liner 3 comprises a removable liner that is disposed on the adhesive portion on the underside of one border of the top dressing cover 1. The second top dressing release liner 3 is removed after removal of a surgical drainage or chest thoracostomy tube. Optionally, the skin surrounding the wound is cleaned before removal of the second top dressing release liner 3.

The first bottom dressing hydrogel 7A comprises a highly absorbent material, where the highly absorbent material is hydrogel, and where the hydrogel is disposed at the interface between the bottom dressing closure carrier 9 and the bottom dressing foam 6.

The bottom dressing foam 6 includes a closed cell foam, where the closed cell foam comprises an airtight and absorbent material that is disposed around a surgical tube, such as a drainage or chest thoracostomy tube, and where a bottom dressing closed cell foam 6 is disposed at the interface between the top dressing closed cell foam 2 and the first bottom dressing hydrogel 7A. The bottom dressing closure layer 9 comprises a carrier material, wherein the carrier material is disposed at the interface between the first bottom dressing hydrogel 7A and the second bottom dressing hydrogel 7B.

The second bottom dressing hydrogel 7B comprises highly absorbent hydrogel material, where the hydrogel is disposed at the interface between the bottom dressing closure layer 9 and the skin surrounding the wound or the wound incision.

The bottom dressing release liner 8 comprises a removable release liner positioned over the second bottom dressing hydrogel 7B in the packaging, where the bottom dressing release liner 8 is removed prior to application of the two-part wound dressing to the wound.

The combined liner 5 comprises a removable combined liner, where the removable combined liner is disposed on the underside of the water-resistant cover 1, wherein the combined liner 5 is removed when the top dressing layer is applied over the bottom dressing layer, and wherein after removal of the combined liner 5 three of the four sides of the top dressing cover are exposed.

In accordance with the present invention, a hydrogel can be formed from a hydrogel precursor derived from any water soluble polymer including: collagen, alginate, agarose, gelatin, fibrin, polyvinyl alcohol (PVA), polyethylene glycol (PEG), PEG-modified collagen-chitosan, polyoxyalkylenes, such as mono-poly(oxyalkylene)-substituted propylene glycol, PEG-modified collagen-chitosan, CF-encapsulated graphene-silk fibroin, chitosan-HCl, k-carrageenan, collagen-PEG, Ca-alginate/polyacrylamide, polyampholyte, di-poly (oxyalkylene)-substituted propylene glycol, mono-poly (oxyalkylene)-substituted trimethylene glycol, di-poly (oxyalkylene)-substituted trimethylene glycol, mono-poly (oxyalkylene)-substituted glycerol, di-poly(oxyalkylene)-substituted glycerol, and tri-poly(oxyalkylene)-substituted glycerol where the poly(oxyalkylene) can be poly(oxyethylene) or soluble poly(oxyethylene-co-oxypropylene); polyacrylates and polymethacrylates, such as poly(acrylic acid), poly(methacrylic acid), poly(hydroxyethylmethacrylate), poly(hydroxyethylacrylate), poly(methylalkylsulfoxide acrylates), poly(methylalkylsulfoxide methacrylates), and copolymers thereof; polyacrylamides and polymethacrylamides, such as poly(acrylamide), poly(methacrylamide), poly (dimethylacrylamide), poly(N-isopropylacrylamide), poly (N-(2-hydroxyethyl)methacrylamide), poly(N-(2-hydroxyethyl)acrylamide), poly(N-(2-hydroxypropyl) methacrylamide), poly(N-(2-hydroxypropyl) methacrylamide) and copolymers thereof; poly(N-vinyl lactam)s, such as poly(vinyl pyrrolidone), poly(vinyl caprolactam), and copolymers thereof; poly(vinyl alcohol); or naturally derived polymers, such as proteins, carboxylated polysaccharides, aminated polysaccharides, glycosaminoglycans, activated polysaccharides, alginic acid, pectinic acid, carboxy methyl cellulose, hyaluronic acid, heparin, heparin sulfate, chitosan, carboxymethyl chitosan, chitin, pullulan, gellan, xanthan, carboxymethyl starch, carboxymethyl dextran. Hydrogel precursors can be linear, branched, dendrimeric, hyperbranched, or star shaped polymers. The hydrogel precursor contains functionality for crosslinking by thermal or photochemical induced reactions.

For the purposes of the invention, the hydrogel precursor can be crosslinked to the hydrogel by formation of ionic or covalent bonds. The crosslinking can be promoted by the addition of a crosslinking reagent to the hydrogel. For example, the crosslinking reagent can be a di- or polyamine and the crosslinking functionality of the hydrogel can be a carboxylic acid or carboxylic acid derivative, for example, an ester, amide, acid anhydride, or imide. In addition to ionic crosslinking via an acid-base reaction, such as a carboxylic acid and an amine, ionic crosslinking can occur by ionic exchange between monovalent ions of the hydrogel precursor and polyvalent ions of the crosslinking reagent. Ionic crosslinking can occur by association of a polycationic or polyanionic hydrogel precursor with a complementary polyanionic or polycationic crosslinking reagent.

In some embodiments of the invention, the hydrogel has a water content of up to 10%, 20%, 30%, 40%, 50%, 60%, 70%, 80%, 90%, or 99.7% w/v.

In preferred embodiments, the hydrogel has a water content of about 30% w/v water and is approximately 0.75 mm thick.

In some embodiments, the top layer dressing comprises a waterproof hydrocolloid to create an airtight and watertight seal around the wound.

In some embodiments, the water-resistant top dressing cover comprises polyurethane.

In some embodiments, the adhesive portion of the top dressing cover 1 adheres the top dressing cover 1 to the top dressing closed cell foam 2, where the adhesive portion of the top dressing cover 1 is any of an acrylate or a silicone-based adhesive.

In some embodiments, the bottom dressing closure layer 9 and the bottom dressing release liner 8 comprise polyethylene.

In some embodiments, the top dressing closed cell foam 2 and the bottom dressing closed cell foam 6 closed cell foam are adapted to provide air-tight seal when applied to multiple surgical drainage and chest thoracostomy tube sizes.

In other aspects, the subject invention discloses a method for using a sterile surgical dressing, including applying a sterile two-part wound dressing to a wound where a surgical tube is applied to the wound, where the two-part wound dressing comprises a top dressing layer, a bottom dressing layer, and a removable combined liner between the top dressing layer and the bottom dressing layer, where the two-part wound dressing comprises a top dressing closed cell foam 2 and a bottom dressing closed cell foam 6, where the top dressing closed cell foam 2 and a bottom dressing closed cell foam 6 are independently wrapped around a surgical tube to form an air-tight seal during surgical tube removal, and where the bottom dressing layer comprises a first bottom dressing hydrogel 7A and a second bottom dressing hydrogel 7B, comprising a highly absorbent material for absorbing exudate from the wound.

In embodiments, the bottom dressing release liner 8 is removed and the dressing is wrapped around the surgical tube through the slits present in each element of the bottom dressing, including the bottom dressing closed cell foam 6, the first bottom dressing hydrogel 7A, the bottom dressing closure carrier 9, and the second bottom dressing hydrogel 7B.

In preferred embodiments, the surgical tube is a chest thoracostomy tube.

In some embodiments, the top dressing closed cell foam 2 and a bottom dressing closed cell foam 6 form an air-tight seal over the wound that inhibits air exchange after surgical tube removal.

In some embodiments, the top dressing closed cell foam 2, the bottom dressing closed cell foam 6 and the first bottom dressing hydrogel 7A and the second bottom dressing hydrogel 7B form an airtight and watertight seal around a surgical tube.

In some embodiments, the second bottom layer hydrogel 7B adheres the bottom dressing layer to skin, contouring to the wound to form an air and watertight seal over the wound.

In some embodiments, the two-part dressing allows removal and exchange of the top layer with retention of the bottom layer, which maintains skin approximation to promote healing.

In some embodiments, any material that contours and prevents or significantly inhibits airflow can be used for the closed cell foam. Any water-resistant covering can be used for the polyurethane covering.

In a most preferred embodiment, the dressing of the subject invention significantly reduces the risk for air exchange during chest thoracostomy tube removal, reducing risk for a post-pull iatrogenic pneumothorax.

In some embodiments, the top dressing layer includes a water-resistant top dressing cover 1 that comprises polyurethane and an adhesive portion; and a top dressing closed cell foam 2 that includes a closed foam cell that comprises an airtight and absorbent sealing material, where the top dressing closed cell foam 2 is disposed around the surgical tube and is disposed underneath and in contact with the top dressing cover 1.

In some embodiments, the dressing is a sterile two-part dressing designed specifically for chest thoracostomy tubes. The dressing comprises two parts: a bottom layer that contains hydrogel with a 30% water content, a polyethylene backing, and polyurethane foam. The top layer comprises polyurethane foam with a polyurethane water-resistant covering.

In some examples, the two-part wound dressing of the subject invention facilitates an improved air-tight and water-resistant seal around a chest tube during tube removal, decreasing the risk of an air leak which can lead to a pneumothorax. The wound dressing is also designed to provide a moist environment over the chest tube wound site with the hydrogel base to promote healing while wicking away excess exudate with the highly absorbent foam that can absorb 20 times its weight in fluid. The dressing also provides a water-resistant covering to limit contamination of the wound during healing.

In some embodiments, the bottom dressing layer comprises an adhesive.

In some examples, the top layer dressing contains a closed-cell foam technology that assists the bottom layer dressing in creating an airtight seal around a chest tube during tube removal.

In some examples, the top layer dressing absorbs exudate from the wound using highly absorbent foam.

Materials and Methods

1. Top dressing cover (for example, Polyurethane cover: 3M 9833) is the outermost portion of the dressing and provides water-resistance properties to the dressing.
2. Top dressing closed cell foam (for example, Freudenberg 3 mm foam) is the closed cell foam on the top portion of the dressing that works in conjunction with the bottom layer foam to sandwich the tube, providing a circumferential airtight seal.
3. Top dressing release liner (for example, Fox River 315 liner) is a release liner on the underside of one border of the 9833 polyurethane top dressing cover. This liner is kept in place to protect the adhesive from contamination of bodily fluids during tube removal. Once the tube is removed the skin is cleaned (if needed), and the release liner is removed to adhere the 9833 to the skin.
4. Top dressing release liner (for example, 9833 carrier paper). This is the carrier paper for the 9833 material that is attached to the top portion of the polyurethane cover. It is cut and left as a border around the dressing to act as a stiffener, inhibiting wrinkles in the polyurethane during application of the dressing to the skin. Once the dressing is applied to the skin, this stiffener is removed (last step in the method).
5. Combined Liner (for example, Fox River 315 Liner). This liner is in place to protect the adhesive on the underside of the polyurethane cover. When applying the top dressing over the bottom dressing, this liner is removed, exposing 3 of the 4 sides of the polyurethane dressing. The remaining side of the polyurethane cover is protected by release liner 3, which will be removed once the chest tube is pulled.
6. Bottom dressing closed cell foam (for example, Freudenberg 3 mm foam). This is the closed cell foam that is located on the bottom dressing. Together with the top layer this will form a circumferential seal around a chest tube.

thick hydrogel layers that will cover the wound and absorb exudate. As they absorb fluid they will form a seal over the incision. They will also keep the wound hydrated, improving wound healing.

8. Bottom dressing release liner (for example, Fox River 315 Liner). This is the release liner that is in place to protect the hydrogel in the packaging and prior to application.
9. Bottom dressing closure layer (for example, Vilmed M1670). This is a carrier material that sits between the two layers of hydrogel to provide some tensile strength support for the hydrogel.

The sterile two-part wound dressing of the subject invention has been designed as a primary dressing for use with surgical tubes to absorb exudate and form an effective seal around the tube. These dressings may also be adopted for use with additional styles of drainage tubes. They are intended to be used under the direction of a healthcare professional and in accordance with the indications for use.

The two-part wound dressing is preferably intended to be used by healthcare professionals or patients under the direction of a healthcare professional.

The two-part wound dressing is intended to be used on patients with one of the following conditions: chest tubes, surgical drainage tubes, feeding tubes, and tracheotomy tubes.

The two-part wound dressing is designed to maintain a tight seal around a chest tube, decreasing the risk for air exchange during tube removal, which may otherwise lead to an iatrogenic pneumothorax.

The two-part wound dressing provides a water-resistant barrier to protect the wound from contamination.

The two-part wound dressing closed cell foam wicks away excess exudate, which may otherwise cause damage to the wound bed or surrounding skin.

The two-part wound dressing hydrogel base provides moisture to promote granulation tissue and healing in the wound.

The two-part wound dressing can be worn for up to 7 days. The dressing should be changed earlier if clinically indicated. The two-part wound dressing is a single-use dressing. Re-use of the dressing may lead to an increased risk of infection or decreased ability to provide an effective seal during tube removal. The two-part wound dressing is MRI safe.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1

Before applying the dressing, the wound is cleansed with an appropriate cleanser and the surrounding skin completely dried. Remove the release liner 8 from the bottom dressing to expose the hydrogel 7B. Using the slits in the dressing, wrap the bottom dressing tightly around the chest tube to create an effective seal. Ensure that the hydrogel covers the entire chest tube wound with overlap onto the surrounding skin.

Once the bottom layer is in place, begin placing the top dressing. Remove the release liner 5 (labeled 1) and place the top dressing over the bottom dressing, ensuring that the top foam 2 completely overlaps the bottom foam 6. Care should be taken to avoid wrinkles in the top dressing during application. The chest tube should exit the dressing in line with the remaining release liner 3 (labeled 2). Using one hand, place firm pressure on the top of the dressing to compress the closed cell foam around the chest tube. Pull to remove the chest tube with the other hand. Using one hand, maintain firm pressure on the dressing. Pull the remaining release liner 3 (labeled 2) with the other hand to expose the adhesive and seal the remaining edge of the dressing to the skin.

If, during tube removal, exudate is deposited on the skin, completely dry this area prior to securing the remaining edge of the dressing to ensure a good seal. Once the dressing is firmly in place and the chest tube has been removed, remove the outer stiffener 4.

All wounds should be inspected regularly. Remove the wound dressing when clinically indicated (i.e., saturated dressing, increased pain) or after a maximum of 7 days. A new complete dressing should be used prior to chest tube removal. If excess drainage from the wound occurs, the two-part dressing system allows for the top dressing to be replaced without removal of the hydrogel base. This will help protect and seal the chest tube wound site during healing. Discard any unused portion of the dressing.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

EXEMPLARY EMBODIMENTS

Embodiment 1. A sterile two-part wound dressing for use with a surgical tube, comprising:

a top dressing layer, a bottom dressing layer, and a combined liner between the top dressing layer and the bottom dressing layer, wherein the top dressing layer comprises:

(a) a first top dressing release liner;

(b) a top dressing cover;

(c) a top dressing closed cell foam;

(d) a second top dressing release liner;

wherein the bottom dressing layer comprises:

(e) a bottom dressing closed cell foam;

(f) a first bottom dressing hydrogel;

(g) a bottom dressing closure carrier;

(h) a second bottom dressing hydrogel;

(i) a bottom dressing release liner;

wherein the bottom dressing layer comprises a highly absorbent material adapted for absorbing exudate that passes through the bottom dressing layer, and wherein the top dressing layer and the bottom dressing layer comprise an airtight sealing material adapted to conform around the surgical tube and to create an air-tight seal when the surgical tube is removed.

Embodiment 2. The two-part wound dressing of embodiment 1, wherein surgical tube is a chest thoracostomy tube.

Embodiment 3. The two-part wound dressing of embodiment 1, wherein the top dressing layer is replaceable.

Embodiment 4. The two-part wound dressing of embodiment 1, wherein the bottom dressing layer comprises an adhesive.

Embodiment 5. The two-part wound dressing of embodiment 1, wherein the top dressing release liner comprises a removable carrier paper contacting a border of the top dressing cover, wherein the top dressing release liner is a stiffener, wherein the top dressing release liner overlaps with a border section around the two-part wound dressing, and wherein the top dressing release liner has slits for easy removal;

wherein the top dressing cover comprises a water-resistant cover, wherein the water-resistant cover comprises an adhesive portion on its underside, wherein the top dressing cover is the outermost portion of the two part dressing, and wherein the top dressing cover is disposed over the top dressing closed cell foam;

wherein the top dressing closed cell foam comprises a closed cell foam, wherein the closed cell foam comprises an airtight and absorbent material, and wherein the top closed cell foam is disposed at an interface between the top dressing cover and the bottom dressing closed cell foam;

wherein the second top dressing release liner comprises a removable second top dressing release liner, wherein the second top dressing release liner is disposed on the underside of one border of the top dressing cover, wherein the one border of the top dressing cover comprises an adhesive portion;

wherein the bottom dressing closed cell foam has an approximately oval or round shape and comprises a closed cell foam, wherein the closed cell foam comprises an airtight sealing material, and wherein the bottom dressing closed cell foam is disposed at an interface between the top dressing closed cell foam and the first bottom dressing hydrogel, and a bottom dressing closed cell foam slit, wherein the length of slit is from about 50% to 80% of the diameter and a width from about 0.01 mm to about 2 mm;

wherein the first bottom dressing hydrogel has an approximately oval or round shape and comprises hydrogel disposed at an interface between the bottom dressing closed cell foam and the bottom dressing closure carrier and a bottom dressing hydrogel slit, wherein a length of the bottom dressing hydrogel slit is from about 50% to 80% of the diameter and a width from about 0.01 mm to about 2 mm;

wherein the bottom dressing closure carrier has an approximately oval or round shape and comprises a carrier material, wherein the carrier material is disposed at an interface between the two hydrogels and a bottom dressing closure carrier slit, wherein a length of the bottom dressing carrier slit is from about 50% to 80% of the diameter and a width from about 0.01 mm to about 2 mm;

wherein the second bottom dressing hydrogel has an approximately oval or round shape and comprises hydrogel configured to contact the wound and skin surrounding the wound and a second bottom dressing hydrogel slit, wherein the length of the second bottom dressing hydrogel slit is from about 50% to 80% of the diameter and a width from about 0.01 mm to about 2 mm;

wherein the bottom dressing release liner has an approximately oval or round shape and comprises a removable release liner positioned over the second bottom dressing hydrogel;

wherein the length and width of each slit is approximately constant through the elements of the bottom dressing layer, and wherein the combined liner comprises a removable combined liner, wherein the removable combined liner is disposed on an underside of the water-resistant cover.

Embodiment 6. The two-part wound dressing of embodiment 1, wherein the hydrogel has a water content of about 30% water and is approximately 0.75 mm thick.

Embodiment 7. The two-part wound dressing of embodiment 1, wherein the water-resistant top dressing cover comprises polyurethane.

Embodiment 8. The two-part wound dressing of embodiment 1, wherein the adhesive portion of the top dressing cover adheres the top dressing cover to the top dressing foam, and wherein the adhesive portion of the top dressing cover is an acrylate or silicone-based adhesive.

Embodiment 9. The two-part wound dressing of embodiment 1, wherein the bottom dressing closure layer and the bottom dressing release liner comprise polyethylene.

Embodiment 10. The two-part wound dressing of embodiment 1, wherein the top dressing closed cell foam and the bottom dressing closed cell foam are configured to provide an air-tight seal when applied to multiple surgical tube sizes.

Embodiment 11. A method for using the wound dressing of embodiment 1, comprising obtaining a wound dressing of embodiment 1, and applying the wound dressing of embodiment 1 to a surgical wound that comprises a surgical tube, by independently wrapping the top dressing closed cell foam and bottom dressing closed cell foam around the surgical tube to form an air-tight seal.

Embodiment 12. The method of embodiment 11, wherein the bottom dressing release liner is removed and the bottom dressing is wrapped around the surgical tube through the slits present in each element of the bottom dressing, including the bottom dressing closed cell foam, the first bottom dressing hydrogel, the bottom dressing closure carrier, and the second bottom dressing hydrogel.

Embodiment 13. The method of embodiment 11, wherein the surgical tube is a chest thoracostomy tube.

Embodiment 14. The method of embodiment 11, wherein the top dressing release liner is removed at the end of the application of the two-part wound dressing.

Embodiment 15. The method of embodiment 11, wherein the closed cell foam is wrapped around the surgical tube.

Embodiment 16. The method of embodiment 11, wherein the second top dressing release liner is removed after the surgical tube is removed; and wherein optionally the skin surrounding the wound is cleaned before removal of the second top dressing release liner.

Embodiment 17. The method of embodiment 11, wherein the bottom dressing release liner is removed prior to the application of the two-part wound dressing to the wound.

Embodiment 18. The method of embodiment 11, wherein the combined liner is removed when the top dressing layer is applied over the bottom dressing layer, and wherein after removal of the combined liner three of four sides of the top dressing cover are exposed.

Embodiment 19. The method of embodiment 11, wherein the second bottom layer hydrogel adheres the bottom dressing layer to the skin surrounding the wound to form an air and watertight seal over the wound.

Embodiment 20. The method of embodiment 11, wherein the top dressing layer is removed and replaced while the bottom dressing layer maintains skin approximation to promote wound healing.

We claim:

1. A sterile two-part wound dressing for use with a surgical tube, comprising:

a top dressing layer, a bottom dressing layer, and a combined liner between the top dressing layer and the bottom dressing layer, wherein the top dressing layer comprises:

(a) a first top dressing release liner;

(b) a top dressing cover;

(c) a top dressing closed cell foam;

(d) a second top dressing release liner;

wherein the bottom dressing layer comprises:

(e) a bottom dressing closed cell foam;

(f) a first bottom dressing hydrogel;

(g) a bottom dressing closure carrier;

(h) a second bottom dressing hydrogel;

(i) a bottom dressing release liner;

wherein the bottom dressing layer comprises an absorbent material adapted for absorbing exudate that passes through the bottom dressing layer, and wherein the top dressing layer and the bottom dressing layer comprise an airtight sealing material adapted to conform around the surgical tube and to create an air-tight seal when the surgical tube is removed.

2. The two-part wound dressing of claim 1, wherein surgical tube is a chest thoracostomy tube.

3. The two-part wound dressing of claim 1, wherein the top dressing layer is replaceable.

4. The two-part wound dressing of claim 1, wherein the bottom dressing layer comprises an adhesive.

5. The two-part wound dressing of claim 1, wherein the top dressing release liner comprises a removable carrier paper contacting a border of the top dressing cover, wherein the top dressing release liner is a stiffener, wherein the top dressing release liner overlaps with a border section around the two-part wound dressing, and wherein the top dressing release liner has release slits for easy removal;

wherein the top dressing cover comprises a water-resistant cover, wherein the water-resistant cover comprises an adhesive portion on its underside, wherein the top dressing cover is the outermost portion of the two part dressing, and wherein the top dressing cover is disposed over the top dressing closed cell foam;

wherein the top dressing closed cell foam comprises a closed cell foam, wherein the closed cell foam comprises an airtight sealing and absorbent material, and wherein the top closed cell foam is disposed at an interface between the top dressing cover and the bottom dressing closed cell foam;

wherein the second top dressing release liner comprises a removable second top dressing release liner, wherein the second top dressing release liner is disposed on the underside of one border of the top dressing cover, wherein the one border of the top dressing cover comprises an adhesive portion;

wherein the bottom dressing closed cell foam has an approximately oval or round shape and comprises a closed cell foam, wherein the closed cell foam comprises an airtight sealing material, and wherein the bottom dressing closed cell foam is disposed at an interface between the top dressing closed cell foam and the first bottom dressing hydrogel layer and a bottom dressing closed cell foam slit, wherein a length of the bottom dressing closed cell foam slit is from about 50% to 80% of the bottom dressing closed cell foam's diameter and has a width of from about 0.01 mm to about 2 mm;

wherein the first bottom dressing hydrogel has an approximately oval or round shape and comprises hydrogel disposed at an interface between the bottom dressing closed cell foam and bottom dressing closure carrier and a bottom dressing hydrogel slit, wherein a length of the bottom dressing hydrogel slit is from about 50% to 80% of the bottom dressing hydrogel's diameter and has a width of from about 0.01 mm to about 2 mm;

wherein the bottom dressing closure carrier has an approximately oval or round shape and comprises a carrier material, wherein the carrier material is disposed at an interface between the two hydrogels and further comprises a bottom dressing closure carrier slit, wherein a length of the bottom dressing layer slit is from about 50% to 80% of the bottom dressing closure layer's diameter and has a width of from about 0.01 mm to about 2 mm;

wherein the second bottom dressing hydrogel has an approximately oval or round shape and comprises hydrogel configured to contact the wound and skin surrounding the wound and further comprises a second bottom dressing hydrogel slit, wherein a length of the second bottom dressing hydrogel slit is from about 50% to 80% of the second bottom hydrogel's diameter and has a width of from about 0.01 mm to about 2 mm;

wherein the bottom dressing release liner has an approximately oval or round shape and comprises a removable release liner positioned over the second bottom dressing hydrogel;

wherein the length and width of each slit is approximately constant through elements of the bottom dressing layer, and wherein the combined liner comprises a removable combined liner, wherein the removable combined liner is disposed on an underside of the water-resistant cover.

6. The two-part wound dressing of claim 1, wherein the hydrogel has a water content of about 30% water and is approximately 0.75 mm thick.

7. The two-part wound dressing of claim 1, wherein the water-resistant top dressing cover comprises polyurethane.

8. The two-part wound dressing of claim 1, wherein an adhesive portion of the top dressing cover adheres the top dressing cover to the top dressing layer foam, and wherein the adhesive portion of the top dressing cover is an acrylate or silicone-based adhesive.

9. The two-part wound dressing of claim 1, wherein the bottom dressing closure layer and the bottom dressing release liner comprise polyethylene.

10. The two-part wound dressing of claim 1, wherein the top dressing closed cell foam and the bottom dressing closed cell foam are configured to provide an air-tight seal when applied to multiple surgical tube sizes.

11. A method for using the wound dressing of claim 1, comprising obtaining a wound dressing of claim 1, and applying the wound dressing of claim 1 to a surgical wound that comprises a surgical tube, by independently wrapping the top dressing closed cell foam and bottom dressing closed cell foam around the surgical tube to form an air-tight seal.

12. The method of claim 11, wherein the bottom dressing release liner is removed and the bottom dressing is wrapped around the surgical tube through a slit present in each element of the bottom dressing, including the bottom dressing closed cell foam, the first bottom dressing hydrogel, the bottom dressing closure carrier, and the second bottom dressing hydrogel.

13. The method of claim 11, wherein the surgical tube is a chest thoracostomy tube.

14. The method of claim 11, wherein the top dressing release liner is removed at the end of the application of the two-part wound dressing.

15. The method of claim 11, wherein the second top dressing release liner is removed after the surgical tube is removed; and wherein optionally the skin surrounding the wound is cleaned before removal of the second top dressing release liner.

16. The method of claim 11, wherein the bottom dressing release liner is removed prior to the application of the two-part wound dressing to the wound.

17. The method of claim 11, wherein the combined liner is removed when the top dressing layer is applied over the bottom dressing layer, and wherein after removal of the combined liner three of four sides of the top dressing cover are exposed.

18. The method of claim 11, wherein the second bottom layer hydrogel adheres the bottom dressing layer to the skin surrounding the wound to form an air and watertight seal over the wound.

19. The method of claim 11, wherein the top dressing layer is removed and replaced while the bottom dressing layer maintains skin approximation to promote wound healing.

* * * * *